United States Patent [19]

Gierhart

[11] Patent Number: 4,485,172

[45] Date of Patent: Nov. 27, 1984

[54] MULTISTAGE PROCESS FOR THE PREPARATION OF FATS AND OILS

[75] Inventor: Dennis L. Gierhart, Linden, N.J.

[73] Assignee: CPC International Inc., Englewood Cliffs, N.J.

[21] Appl. No.: 416,745

[22] Filed: Sep. 10, 1982

Related U.S. Application Data

[63] Continuation of Ser. No. 227,023, Jan. 19, 1981, abandoned.

[51] Int. Cl.$^3$ ................................................ C12P 7/64
[52] U.S. Cl. ..................................... 435/134; 435/244; 435/253; 435/255; 435/921; 435/940; 435/944
[58] Field of Search ............... 426/33, 60, 7; 435/134, 435/163, 184, 244, 249, 253, 255, 921, 940, 944

[56] References Cited

U.S. PATENT DOCUMENTS

| | | | |
|---|---|---|---|
| 3,108,878 | 10/1963 | Higashiuchi et al. | 426/21 |
| 3,293,145 | 12/1966 | Leavitt et al. | 435/872 X |
| 3,445,337 | 5/1969 | Spencer et al. | 435/134 X |
| 4,032,405 | 6/1977 | Tatsumi et al. | 435/134 |
| 4,235,933 | 11/1980 | Moon et al. | 426/60 X |
| 4,308,350 | 12/1981 | Matsuo et al. | 435/134 |

FOREIGN PATENT DOCUMENTS

| | | |
|---|---|---|
| 64483 | 5/1977 | Japan . |
| 64484 | 5/1977 | Japan . |
| 61796 | 5/1980 | Japan . |

OTHER PUBLICATIONS

Deinema, M. H. "Intra-and Extra-Cellular Lipid Production by Yeasts", H. Veenman & Zonen N. V., Wageningen, Netherlands, 1961, pp. 1-54.

*Primary Examiner*—Robert Yoncoskie

[57] ABSTRACT

A process for the production of fats and oils, and particularly fats and oils rich in triglycerides, comprising cultivating microorganisms capable of synthesizing the desired fats and oils to promote growth in a growth medium formulated to contain carbon and nitrogen nutrients and then cultivating the microorganisms in a lipid accumulation medium formulated to include at least one fatty acid containing 10 to 20 carbon atoms.

13 Claims, No Drawings

MULTISTAGE PROCESS FOR THE PREPARATION OF FATS AND OILS

This application is a continuation of application Ser. No. 227,023, filed Jan. 19, 1981, now abandoned.

The present invention relates to a process for the production of fats and oils, and particularly fats and oils rich in triglycerides, from microbial sources.

It is well known that fats and oils can be produced by cultivating an oil-synthesizing microorganism, including algae, bacteria, molds and yeast. Such microorganisms synthesize oils and fats in the oridinary course of their cellular metabolism. Extensive research has been carried out in an effort to identify microorganisms, media and conditions which would permit economically practical oil production.

One field of production of fats and oils by fermentation which has received particular attention is the field of producing cacao butter substitutes. Cacao butter is a naturally-occurring substance which contains large quantities of 1,3-disaturated-2-unsaturated tirglycerides. These triglycerides include 1-stearoyl-2-oleoyl-3-palmitoyl triglycerides and 1,3-dipalmitoyl-2-oleoyl triglycerides. A process for producing triglycerides rich in the foregoing compounds is described in U.S. Pat. No. 4,032,405, granted on June 28, 1977.

As described in this patent, a cacao-butter substitute is produced by cultivating a microorganism from the genus Endomyces, Rhodotorula, Lipomyces or Rhodospordium under aerobic conditions, followed by collecting the cells and isolating the fats and oils rich in 1,3-disaturated-2-unsaturated triglycerides from the cells. The medium employed in the fermentation process of the foregoing patent generally includes a source of assimilable nitrogen, and a carbon source preferably in the form of an aldose or a di- or polysaccharide. The resulting cells are collected and from them is isolated a mixture of the fats and oils which are rich in 1,3-disaturated-2-unsaturated triglycerides.

Improvements in the process as described in the foregoing patent are described in copending application Ser. No. 904,099, filed May 8, 1978, now abandoned. As described in that copending application, it has been found that the yield of the fats and oils can be increased and the distribution of the particular fats and oils can be controlled when the fermentation medium includes a carbon nutrient source in the form of one or more fatty acids containing between 10 and 20 carbon atoms. For example, it has been found that the ratio of saturated to unsaturated acid groups of glyceryl oils may be controlled by employing in the fermentation medium the very acids which form the fatty acid portion of cacao butter, namely palmitic, oleic and stearic acids.

Further improvements in the process described in that application are set forth in copending application Ser. No. 420,462, filed concurrently herewith, wherein it is reported that yields of the desired fats and oils, and particularly fats and oils rich in triglycerides, can be significantly enhanced where the fatty acid is present in the fermentation medium in the form of an emulsion. As is described in the foregoing copending application, the disclosure of which is incorporated herein by reference, it has been found that the use of an emulsion, and particularly one containing particles of the fatty acid having a particle size less than 10 microns, can be effectively utilized by the yeast to produce fats and oils in high yields.

While those processes represent distinct improvements in the art, there is still room for further improvement, particularly in the yield of the fats and oils produced.

It is accordingly an object of this invention to provide a process for the production of fats and oils by fermentation in which the yields of such fats and oils are significantly increased with shortened reaction time.

It is a more specific object of the present invention to provide a process for the production of fats and oils, and particularly fats and oils rich in triglycerides from microbial sources, wherein the yields of saturated fats and oils are increased as compared to prior art processes.

The concepts of the present invention reside in a process for the production of fats and oils, and particularly fats and oils which are rich in triglycerides, wherein yeast cells are grown in a first stage, in a growth medium formulated to contain carbon and nitrogen nutrients followed by cultivation of the yeast cells in an accumulation medium formulated to contain at least one fatty acid consisting of 10–20 carbon atoms. It has been found that the use of a two-stage process significantly increases the production of fats and oils without concommitant increases in undesired side products.

The process of the present invention is particularly well suited for use in the production of fats and oils of the type which are predominant in cacao butter. In accordance with one embodiment of the invention, it has been discovered that the production of such oils can be significantly increased where the lipid accumulation medium is formulated to include palmitic, oleic and stearic acids, preferably in the form of an emulsion as described in copending application Ser. No. 420,462 filed concurrently herewith.

In accordance with the present invention, conditions for rapid growth of the yeast cells in the first stage are optimized and conditions for production of saturated fats in the second stage are optimized separately. Since optimum second stage production conditions for saturated fats are detrimental to rapid growth of the yeast cells, the two stage process provides a significant improvement over previously known techniques.

In the first stage of the process of this invention, the growth-promoting medium is formulated to include both carbon and nitrogen nutrients in proportions such that the yeast cells are still in the logarithmic phase, that is the number of yeast cells increases logarithmically with time to increase the total number of cells present. The logarithmic phase is thus characterized by a high nitrogen to carbon ratio which promotes growth in the cells while minimizing fat accumulation. Then, in the second stage, where fat accumulation is desired, the microorganism, the particular yeast as is described more fully hereinafter, is grown in a medium having a high ratio of carbon to nitrogen nutrient to thereby promote the accumulation of fats and oils.

While the present invention will be described hereinafter with reference to the production of fats and oils of the type which are predominant in cacao butter, that is triglycerides containing 1,3-distearoyl-2-oleoyl triglycerides, 1-stearoyl-2-oleoyl-3-palmitoyl triglycerides and 1,3-dipalmitoyl-2-oleoyl triglycerides, it will be understood by those skilled in the art that the concepts of the present invention may likewise be used in the production of other fats and oils by fermentation.

The microorganisms useful in the practice of this invention may be characterized as oil synthesizing yeasts; such yeasts are well known and available to the art. For example, a number of them are described in U.S. Pat. No. 4,032,405, the disclosure of which is incorporated herein by reference. Particularly preferred for use in the practice of this invention are species from the genus Rhodosporidium, Lipomyces, Candida, Endomyces, Saccharomyces, Rhodotorula, Trichosporon or Torulopsis.

Such oil-synthesizing yeasts are well known and can be isolated by conventional techniques from native sources such as leaves, vegetable stems and the like. It is generally more convenient, however, to obtain such yeasts from various culture storage deposits including, for example the American Type Culture Collection. For economic reasons, it is generally preferred to employ an oil-synthesizing yeast which has a tendency to synthesize and store large amounts of oils. Yeasts having the ability to accumulate 20% oil, and preferably at least 30% oil, on a standard culture medium (such as glucose, ammonium salts and minerals) are generally preferred.

The growth and fermentation media providing nutrients for the cultivation of the particular yeast species to employ depend somewhat on the particular yeast selected for use in the process of this invention. In general, such media are dilute aqueous basic solutions containing carbon and nitrogen nutrient sources, generally in amounts less than 6% by weight based on the weight of the medium. Preferred media are generally adjusted or buffered so that the pH ranges between about 4.0 and 9.0, and preferably 5 to 8.5, as is conventional for optimum yeast cultivation.

As the nitrogen nutrient source, use can be made of any of a variety of conventional nitrogen-containing compounds frequently used as nutrients for microbial growth. Preferred nitrogen compounds include asparagine, glutamine, peptones and the like. In addition, other nitrogen-containing compounds such as ammonium salts and urea may likewise be used.

One nitrogen-containing nutrient which is particularly well suited for use in the practice of this invention is cornsteep, the aqueous liquor formed in the conventional corn-wet-milling process in which dry corn is soaked in warm dilute sulfuric acid. Cornsteep is composed of about 25% by weight of crude protein (8% nitrogen by weight) as well as small amounts of ash, sugars and other beneficial culture constituents. While cornsteep can be used alone as an inexpensive but yet complete nitrogen nutrient source, it can be formulated with other conventional nitrogen nutrient sources well known to those skilled in the art.

The media should also include any one or more of the known essential metabolic mineral salts, including the salts of potassium, sodium, calcium, magnesium, iron or the like. In addition, secondary nutrients such as vitamins and amino acids are likewise desirable, particularly where the cultivation period for the yeast is extensive.

In accordance with the practice of the invention, the ratio of nitrogen to carbon nutrient is 2:1, and preferably 5:1, based on the molar ratio of nitrogen to carbon present in the nutrient medium. It has been found that the source of carbon in the growth stage is preferably at least one carbohydrate. The carbohydrate is generally in the form of an aldose (e.g., glucose, hexose, pentose, etc.) disaccharides such as maltose, sucrose, etc., and oligosaccharides, the latter being preferably derived from the hydrolysis of starch. Polyhydric alcohols are suitably used as well, glycerol being frequently preferred.

In the second stage wherein the fermentation medium is a lipid accumulation medium, the fermentation medium contains a carbon source, generally a predominant amount of one or more fatty acids containing between 10 to 20 carbon atoms. Without limiting the invention as to theory, it is believed that the yeast cells utilize such fatty acids in their metabolism, and thus it is preferred that the fatty acid content of the fatty acid medium constitute at least 10% and preferably 40% or higher of the total carbon source. In that way, the fatty acids, to the extent they serve to modify the metabolism of the yeast cells to produce triglyceride oils having a particular fatty acid content, are not masked by the presence of other carbon nutrient sources in the lipid accumulation medium. As already noted, the lipid accumulation stage is characterized by a high carbon to nitrogen ratio; in general, the ratio of carbon to nitrogen in the second stage is greater than about 10:1 and preferably greater than about 50:1.

The fatty acid or acids employed as the carbon source in the practice of this invention may be obtained from any of a variety of known sources. For example, palmitic acid ($C_{16}:0$), stearic acid ($C_{18}:0$) or oleic acid ($C_{18}:1$) can be obtained commercially, either in the form of the free acid or salts such as the sodium salt. These more common fatty acids can be employed alone or in mixture with others. Polyunsaturated fatty acids, such as linoleic acid ($C_{18}:2$), linolenic acid ($C_{18}:3$), and other fatty acids containing 16 to 20 carbon atoms may also be obtained in pure form but are more readily available in the less expensive form of commercial mixtures, such as soap stock.

The composition of the fatty acid employed is important to the extent that each fatty acid causes a unique type of shift in the oil-synthesizing metabolism of a given yeast species. When use is made of a mixture of fatty acids, their combined effect is an interaction to result in the metabolic mixtures of triglycerides containing the various fatty acids present in the fermentation medium.

However, accurate prediction of the precise yield in oil composition to be obtained from any particular fatty acid carbon source is largely empirically based. Conventional analytical procedures permit the determination of the yield in composition of oils produced from any particular carbon sources, and hence routine experimentation permits the ready identification of fatty acid carbon sources suitable for the production of any particular oil.

Some generalizations in the form of general rules have been determined, however. For example, the presence of a fatty acid of any given carbon length in the carbon source ordinarily results in the increase in the proportion of triglyceride esters containing that fatty acid as a component of the triglyceride. Similarly, the degree of saturation and/or unsaturation (and particularly polyunsaturation) in the oil produced is directly related to the corresponding saturation level of the fatty acid composition employed as the carbon source. Thus, the use of palmitic, oleic and stearic acids as the carbon source promote the formation of oils which closely approximate those existing in cacao butter.

The conditions under which the yeast is cultivated to produce fats and oils in accordance with the process of this invention are not different from those generally employed in prior art fermentation systems. In general, the yeast employed in the practice of this invention to produce such fats and oils are generally the same as prior art processes employing the same type yeast species.

The temperature at which the fermentation is carried out is generally within the range of about 20 to 40 C., with higher temperatures within that range favoring the production of saturated oils while lower temperatures within the range favor the production of unsaturated oils.

Similarly, oxygen may have some effect on the growth of the yeast cells. In general, it has been found that aerobic cultivation of the yeast cells increases the final yield of the oil produced by the microorganisms.

Once the fermentation has been allowed to carry out for the desired period of time, generally for one to seven days and preferably less than five days, the yeast cells are separated from the fermentation media by conventional means and their oil content removed. For example, the cells can first be subjected to rupture by, for example, freezing or hydrolysis, and then the oil extracted from the debris with a suitable solvent, preferably a volatile solvent to facilitate subsequent removal of the solvent from the oil.

As noted above, it is an important concept of the invention that the fatty acids present in the lipid accumulation medium be in emulsified form. That is preferably accomplished by addition to the fermentation medium of an emulsifier which is compatible with the fatty acids employed and which does not adversely affect the metabolism of the yeast cells. In general, emulsifiers employed in the practice of this invention are ionic and non-ionic emulsifiers having an HLB above 15.

Preferred for this purpose are emulsifiers in the form of fatty acid derivatives of sorbitol and sorbitol anhydrides. Particularly preferred are non-ionic emulsifiers such as those marketed by Atlas Chemical Industries Inc. under the trademark "Tween", which are polyoxyethylene derivatives of fatty acid partial esters of sorbitol anhydrides, and those marketed under the trademark "Span", which are fatty acid partial esters of sorbitol anhydrides. Both types of emulsifiers are approved by the FDA for food use; it has surprisingly been found that they do not adversely affect the metabolism of the yeast cells in the formation of fats and oils.

In general, only enough of the emulsifier as is sufficient to emulsify the fatty acids present in the lipid accumulation medium need be used. In general, that amount ranges from 0.0001% to 1% based on the weight of the fermentation medium. The emulsion is preferably produced by adding the emulsifier to the fatty acid or fatty acids and then providing sufficient agitation to produce a substantially homogeneous medium, either with or without the other components of the medium having been added at the time of the agitation.

In the preferred practice of the invention, the emulsion is formed by heating the fatty acid with a buffer to a pH ranging from 7 to 9, followed by autoclaving the fatty acid to sterilize it if necessary. Then the emulsifier is added and the resulting mixture homogenized. The emulsion is next subjected to rapid cooling at a rate sufficient to crystalize stearic acid particles of very small sizes. It has been found in accordance with the practice of the invention that particle sizes less than 10 microns are particularly suitable to insure that the fatty acid or acids are utilized effectively in the lipid accumulation medium.

Having described the basic concepts of the present invention, reference is now made to the following examples, which are provided by way of illustration and not by way of limitation, of the practice of the present invention. In those examples, all of the percentages are percentages by weight unless otherwise indicated.

EXAMPLE 1

This example illustrates the practice of the invention utilizing a two-stage process and stearic acid as the carbon-nutrient source.

Yeast cells of R. toruloides were grown in a 500 ml flask containing the following growth medium:

| | |
|---|---|
| Glucose | 5% |
| Peptone | 5% |
| Yeast extract | 1% |
| Water | 300 ml |

The pH of the growth medium was 5.0 and growth was allowed to continue until the late logarithmic stage (i.e., no fat accumulation).

The cells were then harvested and added to a series of emulsions at a 1:1 cell/lipid ratio (dry weight). The emulsion had been prepared in a Teckmar Homogenizer. The control fermentation medium (Sample A) had the following composition:

| | |
|---|---|
| Stearic acid | 1% |
| $K_2HPO_4$ | 1% |
| Emulsifier (Tween 20) | 0.01% |
| Antibiotic | 10 μg/ml |
| Water | 100 ml |

Samples B to F were formulated with the same composition, except that they also included additives as follows:

| | | |
|---|---|---|
| Sample B | Control | 0.1% glucose |
| Sample C | Control | 0.5% glucose |
| Sample D | Control | 1.0% glucose |
| Sample E | Control | 0.2% glycerol |
| Sample F | Control | 0.1% sterculic acid |

The fermentation of Samples A to F was carried out at an initial pH of 8.0 and a temperature of 28 C. for 3 days in a shake flask at 200 rpm. Then the oil was recovered as described in Example 1 and submitted for analysis.

The following results were obtained.

TABLE 1

RESULTS - Example 1

| Sample | A-Control | B | | C | | D | | E | | F |
|---|---|---|---|---|---|---|---|---|---|---|
| Mg. of Neutral Oil | 270 mg. | *520 | 467 | *528 | 204 | 180 | *524 | *511 | 433 | *411 |
| % Conversion based on lipid | 27% | 52% | 47% | 53% | 20% | 18% | 52% | 51% | 43% | 41% |
| C:12 | — | — | — | — | — | .3 | — | .5 | .1 | .1 |
| C:14 | 0.4 | .5 | .5 | .5 | .5 | .6 | .4 | .6 | .3 | .4 |
| C:16:0 | 10.5 | 11.5 | 13.8 | 13.3 | 13.4 | 14.9 | 10.7 | 12.1 | 9.7 | 11.3 |

TABLE 1-continued

| Sample | A-Control | B | | C | | D | E | | F |
|---|---|---|---|---|---|---|---|---|---|
| C:16:1 | 0.3 | 1.0 | .3 | .5 | 1.8 | 2.4 | 1.6 | .5 | 2.2 | .4 |
| C:18:0 | 39.3 | 42.2 | 39.0 | 40.2 | 38.6 | 23.8 | 32.4 | 36.6 | 29.4 | 53 |
| C:18:1 | 38.3 | 35.2 | 36.5 | 36.0 | 32 | 41.9 | 41.5 | 39.2 | 44.3 | 25.4 |
| C:18:2 | 6.1 | 0.9 | .7 | 1.0 | .6 | 5.2 | 7.7 | 3.5 | 7.7 | 3.2 |
| C:20 | 0.5 | 0.6 | .6 | .6 | .5 | .5 | .5 | .6 | .5 | .6 |
| C:18:3 | 1.4 | 0.1 | .1 | .1 | .1 | .8 | 2.2 | .5 | 1.7 | .6 |
| C:22 | 0.3 | .4 | .5 | .4 | .5 | .6 | .4 | .5 | .6 | .4 |
| Unknowns | 2.7 | 7.3 | 7.6 | 7.0 | 11.2 | 8.0 | 2.4 | 4.8 | 2.8 | 4.5 |
| Total saturates | 50.1 | 55.5 | 54.6 | | 54.5 | 41.8 | 44.6 | 51.6 | 41.2 | 66.0 |
| Total monounsaturates | 38.6 | 36.2 | 36.7 | 36.5 | 33.6 | 44.3 | 43.1 | 39.6 | 46.5 | 25.7 |
| Total polyunsaturates | 7.5 | 1.0 | .9 | 1.2 | .8 | 5.9 | 9.8 | 3.9 | 9.4 | 3.7 |
| Theoretical Iodine # | | 33 | 33 | 34 | 30.4 | 49 | 56 | 41 | 57 | 29 |

*Values used for comparison.

As shown by the foregoing data, the addition of small amounts of carbohydrates and/or glycerol results in increased conversion efficiency. 0.1% added glucose or glycerol resulted in maximum conversions and further increases in glucose level did not increase conversions further, but actually began to decrease efficiency when conversions were calculated on lipid and sugar as substrate. Sterculic acid also appeared to increase conversions.

A low level of glucose (0.1 to 0.5%) addition resulted in very slight increases in palmitic and stearic levels at the expense of oleic and linoleic, while 1% added glucose resulted in slightly increased desaturation at the expense of stearic acid. It appears as though glycerol may slightly stimulate desaturation. The addition of small amounts of sterculic acid resulted in greatly reduced desaturase activity and increased stearic acid levels.

EXAMPLE 2

This example illustrates a two-stage process of the invention in which the fermentation time was varied.

Cells grown as described in Example 1 were harvested centrifugally and placed in a series of emulsions at a 1:1 cell/lipid ratio. Each emulsion had the following composition:

| | |
|---|---|
| Lipids | 1% |
| Stearic acid | 0.7% |
| Palmitic acid | 0.3% |
| K$_2$HPO$_4$ | 0.1% |
| Emulsifier | 3 drops |

Fermentation flasks contained 200 ml and were incubated at 200 rpm at 32 C.; the pH was maintained at 8.0.

Cells were harvested at 20 hours and 2, 3, 5, 7, 9 and 11 days. The oils were recovered and subjected to analysis. The following results were obtained.

TABLE 2

RESULTS

| Fermentation Time (hrs.) | 20 | | 48 | | 72 | | 120 | | 168 | 216 | | 264 | |
|---|---|---|---|---|---|---|---|---|---|---|---|---|---|
| % Conversion to neutral oil | 25 | 25 | 37 | 41 | 37 | 37 | 28 | 29 | 27 | 30 | 25 | 21 | 16 | 13 |
| % Triglyceride | 97.1 | | | | 92.2 | 89.8 | 85.1 | 89.8 | * | 89 | 87 | * | 75 | * |
| Unknown | — | — | — | — | — | — | — | — | | — | — | | — | |
| C:10 | — | — | — | — | — | — | — | — | | — | — | | — | |
| C:12 | — | — | — | — | — | .1 | — | .1 | | — | — | | — | |
| C:14 | .6 | | .5 | | .4 | .5 | .4 | .5 | | .5 | .3 | | .4 | |
| Unknown | .2 | | .2 | | .1 | .1 | — | .1 | | — | — | | .1 | |
| Unknown | — | | — | | — | — | — | .1 | | — | — | | — | |
| C:16 | 27 | | 21.7 | | 19.8 | 20 | 20.5 | 20.2 | | 20.8 | 18.3 | | 18.7 | |
| C16:1 | 1.9 | | 1.2 | | 1.1 | 1 | 1.2 | 1.1 | | 1.1 | 1.1 | | 1.8 | |
| Unknown | 2.0 | | 1.9 | | 1.9 | 2 | 1.8 | 1.9 | | 1.9 | 1.8 | | 1.1 | |
| Unknown | 1 | | .7 | | .6 | .6 | .6 | .7 | | .5 | .6 | | .6 | |
| C:18 | 16.3 | | 30.7 | | 29.8 | 28.6 | 30.5 | 28.2 | | 23.7 | 28.1 | | 22.9 | |
| C18:1 | 46.2 | | 38.5 | | 40 | 42.2 | 40.9 | 41.4 | | 47.7 | 42.6 | | 46.6 | |
| C18:2 | 3.3 | | 3.2 | | 3.2 | 3.5 | 2.7 | 3.9 | | 2.7 | 5.2 | | 6.2 | |
| C20 | .4 | | .6 | | .5 | .6 | .5 | .9 | | .4 | .7 | | .6 | |
| C18:3 | — | | .2 | | .6 | .3 | — | — | | — | .5 | | .2 | |
| Unknown | .4 | | .2 | | 1.8 | — | — | .24 | | — | — | | — | |
| C:22 | | | .5 | | .4 | .6 | .7 | .7 | | .7 | .7 | | .7 | |

*triglyceride is % of neutral oil

In this example, 20 hours after initial second-stage incubation, the palmitic level was high, while the stearic level was relatively low. At 20 hours, the conversion was only partially completed. At 48 hours, the palmitic level and oleic levels decreased, while the stearic increased. At 48 hours, the composition approached cocoa butter, and the conversion level had also been maximized. From that point on, the conversion efficiency gradually decreased, while the composition remained remarkably similar. The percent triglycerides within the neutral oil was also highest at 48 hours and remained rather consistently around the 90% level. By the last day, the conversion rate, % triglycerides, palmitic and stearic levels had all fallen slightly, while the oleic and linoleic levels had increased slightly. The results suggest that once triglycerides are synthesized and stored, they are altered little, but are slowly metabolized for maintenance energy.

EXAMPLE 3

This illustrates a two-stage process of the invention to produce oils similar to those of cocoa butter.

Using the procedure of Example 2, yeast cells were grown, harvested and added at a 1:1 cell/lipid ratio to a series of emulsions.

A series of emulsions were prepared having the following composition:

| Lipids | 1% |
|---|---|
| Emulsifier (Tween 20) | 0.01% |
| Glycerol | 0.2% |
| K$_2$HPO$_4$ | 0.1% |
| Palmitic/stearic (45/55) | |
| pH 6.5 | |

Sample (A) incubated in flasks at 200 rpm at 32 C. for 72 hours with volume of 200 ml (B) Same as A only incubated with *Lipomyces Starkeyii*

(C) Same as A only agitation increased to 300 rpm and volume decreased to 100 ml and completed in 48 hours and no glycerol (D) Same as C only lipids increased to 3% and Tween 20 increased to 0.03%

(E) Same as D only 0.6% carbohydrate added

TABLE 3

Results Example 3

| FAC | A | B | C | D | E |
|---|---|---|---|---|---|
| | | | % conversion to triglyceride | | |
| | 60% | 37% | 47% | 36% | 45% |
| C:12 | — | — | — | .1 | .1 |
| C:14 | .5 | .3 | .3 | .4 | .4 |
| C:16 | 22. | 42. | 25. | 35.3 | 31.2 |
| C:16:1 | 1.3 | 5.0 | 2.5 | 2.1 | 2.2 |
| unknown | 1.9 | 2.4 | 1.4 | 1.7 | 1.8 |
| C:18 | 30 | 10.5 | 14 | 9.8 | 13.1 |
| C:18:1 | 37 | 38.4 | 47.4 | 45. | 45.8 |
| C:18:2 | 5.1 | 1.0 | 6.4 | 3.2 | 2.9 |
| C:20 | .5 | 0.1 | .4 | .3 | .4 |
| C:18:3 | .6 | 0.2 | .6 | .3 | .3 |

It was observed that sample A had a conversion rate of 60% and the fatty acid content was quite similar to cocoa butter. Sample B which used a different organism (*L. Starkeyii*) did not have a similar composition demonstrating some differences among various yeasts.

Samples C, D, and E were fattened under a greater aeration/agitation rate (smaller volume, greater RPM) and demonstrate a distinct decrease in stearate level demonstrating that these factors also can control FAC of resultant butters.

It will be understood that various changes and modifications can be made in the details of formulation, procedure and processing without departing from the spirit of the invention, especially as defined in the following claims.

I claim:

1. A process for the production of fats and oils comprising the steps of:
   (a) cultivating a microorganism capable of synthesizing fats or oils in a suitable growth medium containing a source of assimilable nitrogen and a source of assimilable carbon with the ratio of nitrogen to carbon being such that the microorganism is grown in its logarithmic phase,
   (b) harvesting the microorganism thus grown, and
   (c) cultivating the cells of said microorganism in a lipid accumulation medium in the form of an emulsion comprising a carbon nutrient source having a fatty acid component, selected from the group consisting of palmitic, oleic and stearic acids and mixtures thereof, wherein the relative concentrations of said acids are selected to produce triglycerides characteristically found in cocoa butter, to promote the production of fats or oils within the cells of said microorganism in the form of 1,3-disaturated-2-unsaturated triglycerides characteristically found in cocoa butter.

2. A process as defined in claim 1 wherein the growth medium contains at least one carbohydrate.

3. A process as defined in claim 2 wherein said carbohydrate is a saccharide.

4. A process as defined in claim 1 wherein the yeast cells are cultivated aerobically.

5. A process as defined in claim 1 wherein the fatty acid component has a particle size less than 10 microns.

6. A process as defined in claim 1 wherein the fatty acid component has been emulsified with an emulsifying agent hving an HLB greater than 15.

7. A process for the production of fats and oils in the form of 1,3-disaturated-2-unsaturated triglycerides characteristically found in cocoa butter comprising the steps of:
   (a) cultivating a microorganism capable of synthesizing fats or oils in the form of 1,3-disaturated triglycerides in a suitable growth medium containing a source of assimilable nitrogen and a source of assimilable carbon, with the ratio of nitrogen to carbon being such that the microorganism is grown in its logarithmic phase,
   (b) harvesting the microorganism thus grown, and
   (c) cultivating the cells of said microorganism in a lipid accumulation medium in the form of the an emulsion having a fatty acid component comprising at least one fatty acid having from 10 to 20 carbon atoms to promote the production of fats or oils within the cells of said microorganism.

8. A process as defined in claim 1 or 7 in which the microorganism cultivated is a yeast.

9. A process as defined in claim 8 in which the yeast is a specie of the genus selected from the group consisting of Rhodosporidium, Lipomyces, Candida, Endomyces, Saccharomyces, Rhodotorula, Trichosporon and Torulopsis.

10. A process as defined in claim 8 wherein the yeast comprises *R. toruloides* and *Lipomyces starkeyii*.

11. A process as defined in claim 8 wherein the yeast comprises *R. toruloides*.

12. A process as defined in claim 7 wherein the fatty acid component has been emulsified with an emulsifying agent having an HLB greater than 15.

13. A process as defined in claim 7 wherein the fatty acid component comprises a mixture of stearic, palmitic and oleic acid.

* * * * *